United States Patent [19]

Henry

[11] Patent Number: 5,130,087

[45] Date of Patent: * Jul. 14, 1992

[54] FATIGUE CRACK RESISTANT NICKEL BASE SUPERALLOYS

[75] Inventor: Michael F. Henry, Schenectady, N.Y.

[73] Assignee: General Electric Company, Schenectady, N.Y.

[ * ] Notice: The portion of the term of this patent subsequent to Jan. 8, 2008 has been disclaimed.

[21] Appl. No.: 560,413

[22] Filed: Jul. 30, 1990

Related U.S. Application Data

[62] Division of Ser. No. 292,805, Jan. 3, 1989, Pat. No. 4,983,233.

[51] Int. Cl.$^5$ .............................................. C22C 19/05
[52] U.S. Cl. ................................... 420/448; 148/428
[58] Field of Search ................. 420/448; 148/404, 434

[56] References Cited

U.S. PATENT DOCUMENTS

| | | | |
|---|---|---|---|
| 3,061,426 | 10/1962 | Bieber | 420/448 |
| 3,589,893 | 6/1971 | Lund et al. | 420/448 |
| 3,825,420 | 7/1974 | Ewing et al. | 420/448 |
| 3,902,862 | 9/1975 | Moll et al. | 420/448 |
| 4,207,098 | 6/1980 | Shaw | 420/448 |

FOREIGN PATENT DOCUMENTS

| | | |
|---|---|---|
| 260511 | 8/1987 | European Pat. Off. . |
| 240451 | 10/1987 | European Pat. Off. . |
| 248757 | 12/1987 | European Pat. Off. . |
| 292320 | 11/1988 | European Pat. Off. . |
| 1458421 | 12/1964 | Fed. Rep. of Germany . |
| 1810246 | 11/1968 | Fed. Rep. of Germany . |
| 1418583 | 12/1964 | France . |
| 1552873 | 12/1968 | France . |
| 61-79742 | 4/1986 | Japan . |
| 1075216 | 7/1967 | United Kingdom . |
| 1261403 | 1/1972 | United Kingdom . |
| 2151659 | 12/1983 | United Kingdom . |

OTHER PUBLICATIONS

G. W. Meetham, "Development of Gas Turbine Materials", Applied Science Publishers, London, Great Britain (1981) pp. 296-298.

*Primary Examiner*—R. Dean
*Assistant Examiner*—Margery S. Phipps
*Attorney, Agent, or Firm*—Paul E. Rochford; James C. Davis, Jr.; James Magee, Jr.

[57] ABSTRACT

The present invention provides an alloy having improved crack growth inhibition and having high strength at high temperatures. The composition of the alloy is essentially as follows:

| Ingredient | Concentration in Weight % Claimed Composition | |
|---|---|---|
| | From | To |
| Ni | balance | |
| Co | 4 | 12 |
| Cr | 7 | 13 |
| Mo | 2 | 6 |
| Al | 3.0 | 6.0 |
| Ti | 3.5 | 5.0 |
| Ta | 2.0 | 4.0 |
| Nb | 1.0 | 3.0 |
| Re | 0.0 | 3.0 |
| Hf | 0.0 | 0.75 |
| Zr | 0.0 | 0.10 |
| V | 0.0 | 3.0 |
| C | 0.0 | 0.20 |
| B | 0.0 | 0.10 |
| W | 0.0 | 1.0 |
| Y | 0.0 | 0.10. |

3 Claims, 13 Drawing Sheets

FATIGUE CRACK RESISTANT NICKEL BASE SUPERALLOYS

This application is a division of application Ser. No. 07/292,805, filed Jan. 3, 1989 now U.S. Pat. No. 4,983,233.

RELATED APPLICATIONS

The subject application relates generally to the subject matter of application Ser. No. 907,550, filed Sep. 15, 1986 now U.S. Pat. No. 4,816,084 as well as to Ser. No. 080,353, filed Jul. 31, 1987 abandoned, and its continuation, Ser. No. 363,734, filed Jun. 9, 1989. It also relates to Ser. Nos. 103,851, (now U.S. Pat. No. 4,867,812), 103,996 and 104,001, filed Oct. 2, 1097. Further, it relates to Ser. No. 250,204, filed Aug. 28, 1988; Ser. No. 248,756, filed Sep. 26, 1988; Ser. No. 250,205, filed Sep. 28, 1988; Ser. No. 248,755, filed Sep. 26, 1988; and to Ser. No. 248,754, filed Sep. 26, 1988. The texts of the related applications and of the applications referenced therein are incorporated herein by reference.

BACKGROUND OF THE INVENTION

It is well known that nickel based superalloys are extensively employed in high performance environments. Such alloys have been used extensively in jet engines, in land based gas turbines and other machinery where they must retain high strength and other desirable physical properties at elevated temperatures of a 1000° F. or more.

Many of these alloys contain a $\gamma'$ precipitate in varying volume percentages. The $\gamma'$ precipitate contributes to the high performance properties of such alloys at their elevated us temperatures.

More detailed characteristics of the phase chemistry of $\gamma'$ are given in "Phase Chemistries in Precipitation-Strengthening Superalloy" by E. L. Hall, Y. M. Kouh, and K. M. Chang [Proceedings of 41st Annual Meeting of Electron Microscopy Society of America, August 1983 (p. 248)].

The following U.S. patents disclose various nickel-base alloy compositions: U.S. Pat. No. 2,570,193; U.S. Pat. No. 2,621,122; U.S. Pat. No. 3,046,108; U.S. Pat. No. 3,061,426; U.S. Pat. No. 3,151,981; U.S. Pat. No. 3,166,412; U.S. Pat. No. 3,322,534; U.S. Pat. No. 3,343,950; U.S. Pat No. 3,575,734; U.S. Pat. No. 3,576,861; U.S. Pat. No. 4,207,098 and U.S. Pat. No. 4,336,312. The aforementioned patents are representative of the many alloying developments reported to date in which many of the same elements are combined to achieve distinctly different functional relationships between the elements such that phases providing the alloy system with different physical and mechanical characteristics are formed. Nevertheless, despite the large amount of data available concerning the nickel-base alloys, it is still not possible for workers in the art to predict with any significant degree of accuracy the physical and mechanical properties that will be displayed by certain concentrations of known elements used in combination to form such alloys even though such combination may fall within broad, generalized teachings in the art, particularly when the alloys are processed using heat treatments different from those previously employed.

A problem which has been recognized to a greater and greater degree with many such nickel based superalloys is that they are subject to formation of cracks or incipient cracks, either in fabrication or in use, and that the cracks can actually propagate or grow while under stress as during use of the alloys in such structures as gas turbines and jet engines. The propagation or enlargement of cracks can lead to part fracture or other failure. The consequence of the failure of the moving mechanical part due to crack formation and propagation is well understood. In jet engines it can be particularly hazardous.

U.S. Pat. No. 4,685,977, entitled "Fatigue-Resistant Nickel-Base Superalloy and Method" is assigned to the same assignee as the subject application. It discloses an alloy having a superior resistance to fatigue crack propagation based on alloy chemistry, $\gamma'$ precipitate content and grain structure. A method of alloy preparation is also taught.

However, what has been poorly understood until recent studies were conducted was that the formation and the propagation of cracks in structures formed of superalloys is not a monolithic phenomena in which all cracks are formed and propagated by the same mechanism and at the same rate and according to the same criteria. By contrast the complexity of the crack generation and propagation and of the crack phenomena generally and the interdependence of such propagation with the manner in which stress is applied is a subject on which important new information has been gathered in recent years. The variability from alloy to alloy of the effect of the period during which stress is applied to a member to develop or propagate a crack, the intensity of the stress applied, the rate of application and of removal of stress to and from the member and the schedule of this application was not well understood in the industry until a study was conducted under contract to the National Aeronautics and Space Administration. This study is reported in a technical report identified as NASA CR-165123 issued from the National Aeronautics and Space Administration in August 1980, identified as "Evaluation of the Cyclic Behavior of Aircraft Turbine Disk Alloys" Part II, Final Report, by B. A. Cowles, J. R. Warren and F. K. Hauke, and prepared for the National Aeronautics and Space Administration, NASA Lewis Research Center, Contract NAS3-21379.

A principal finding of the NASA sponsored study was that the rate of propagation based on fatigue phenomena or in other words, the rate of fatigue crack propagation (FCP), was not uniform for all stresses applied nor to all manners of applications of stress. More importantly, the finding was that fatigue crack propagation actually varied with the frequency of the application of stress to the member where the stress was applied in a manner to enlarge the crack. More surprising still, was the magnitude of the finding from the NASA sponsored study that the application of stress of lower frequencies rather than at the higher frequencies previously employed in studies, actually increased the rate of crack propagation. In other words the NASA study verified that there was a time dependence in fatigue crack propagation. Further the time dependence of fatigue crack propagation was found to depend not on frequency alone but on the time during which the member was held under stress or a so-called hold-time.

Following the documentation of this unusual degree of increased fatigue crack propagation at lower stress frequencies there was some belief in the industry that this newly discovered phenomena represented an ultimate limitation on the ability of the nickel based superalloys to be employed in the stress bearing parts of the turbines and aircraft engines and that all design effort had to be made to design around this problem.

However, it has been discovered that it is feasible to construct parts of nickel based superalloys for use at high stress in turbines and aircraft engines with greatly reduced crack propagation rates and with good high temperature strength.

It is known that the most demanding sets of properties for superalloys are those which are needed in connection with jet engine construction. Of the sets of properties which are needed those which are needed for the moving parts of the engine are usually greater than those needed for static parts, although the sets of needed properties are different for the different components of an engine.

Because some sets of properties are not attainable in cast alloy materials, resort is sometimes had to the preparation of parts by powder metallurgy techniques. However, one of the limitations which attends the use of powder metallurgy techniques in preparing moving parts for jet engines is that of the purity of the powder. If the powder contains impurities such as a speck of ceramic or oxide the place where that speck occurs in the moving part becomes a latent weak spot where a crack may initiate. Such a weak spot is in essence a latent crack. The possible presence of such latent cracks makes the problems of reducing and inhibiting the crack propagation rate all the more important. I have found that it is possible to inhibit crack propagation both by the control of the composition of alloys and by the methods of preparation of such metal alloys.

Pursuant to the present invention, a superalloy which can be prepared by powder metallurgy techniques is provided. Also a method for processing this superalloy to produce materials with a superior set or combination of properties for use in advanced engine disk applications is provided. The properties which are conventionally needed for materials used in disk applications include high tensile strength and high stress rupture strength. In addition the alloy of the subject invention exhibits a desirable property of resisting time dependent crack growth propagation. Such ability to resist crack growth is essential for the component LCF life.

As alloy products for use in turbines and jet engines have developed it has become apparent that different sets of properties are needed for parts which are employed in different parts of the engine or turbine. For jet engines the material requirements of more advanced aircraft engines continue to become more strict as the performance requirements of the aircraft engines are increased. The different requirements are evidenced, for example, by the fact that many blade alloys display very good high temperature properties in the cast form. However, the direct conversion of cast blade alloys into disk alloys is very unlikely because blade alloys display inadequate strength at intermediate temperatures. Further, the blade alloys have been found very difficult to forge and forging has been found desirable in the fabrication of disks from disk alloys. Moreover, the crack growth resistance of disk alloys has not been evaluated. Accordingly to achieve increased engine efficiency and greater performance, constant demands are made for improvements in the strength and temperature capability of disk alloys as a special group of alloys for use in aircraft engines.

Accordingly what was sought in undertaking the work which lead to the present invention was the development of a disk alloy having a low or minimum time dependence of fatigue crack propagation and moreover a high resistance to fatigue cracking. In addition what was sought was a balance of properties and particularly of tensile, creep and fatigue properties. Further what was sought was an enhancement of established alloy systems relative to inhibition of crack growth phenomena.

The development of the superalloy compositions and methods of their processing of this invention focuses on the fatigue property and addresses in particular the time dependence of crack growth.

Crack growth, i.e., the crack propagation rate, in high-strength alloy bodies is known to depend upon the applied stress ($\sigma$) as well as the crack length (a). These two factors are combined by fracture mechanics to form one single crack growth driving force; namely, stress intensity factor K, which is proportional to $\sigma\sqrt{a}$. Under the fatigue condition, the stress intensity in a fatigue cycle may consist of two components, cyclic and static. The former represents the maximum variation of cyclic stress intensity ($\Delta K$), i.e., the difference between $K_{max}$ and $K_{min}$. At moderate temperatures, crack growth is determined primarily by the cyclic stress intensity ($\Delta K$) until the static fracture toughness $K_{IC}$ is reached. Crack growth rate is expressed mathematically as $da/dN \propto (\Delta K)^n$. N represents the number of cycles and n is material dependent. The cyclic frequency and the shape of the waveform are the important parameters determining the crack growth rate. For a given cyclic stress intensity, a slower cyclic frequency can result in a faster crack growth rate. This undesirable time-dependent behavior of fatigue crack propagation can occur in most existing high strength superalloys. To add to the complexity of this time-dependence phenomenon, when the temperature is increased above some point, the crack can grow under static stress of some intensity K without any cyclic component being applied (i.e. $\Delta K = 0$). The design objective is to make the value of da/dN as small and as free of time-dependency as possible. Components of stress intensity can interact with each other in some temperature range such that crack growth becomes a function of both cyclic and static stress intensities, i.e., both $\Delta K$ and K.

BRIEF DESCRIPTION OF THE INVENTION

It is, accordingly, one object of the present invention to provide nickel-base superalloy products which are more resistant to cracking.

Another object is to provide a method for reducing the tendency of known and established nickel-base superalloys to undergo cracking.

Another object is to provide articles for use under cyclic high stress which are more resistant to fatigue crack propagation.

Another object is to provide a composition and method which permits nickel-base superalloys to have imparted thereto resistance to cracking under stress which is applied cyclically over a range of frequencies.

Other objects will be in part apparent and in part pointed out in the description which follows.

In one of its broader aspects, objects of the invention can be achieved by providing a composition of the following approximate content:

| Ingredient | Concentration in Weight % Claimed Composition | |
| --- | --- | --- |
| | From | To |
| Ni | balance | |
| Co | 4 | 12 |
| Cr | 7 | 13 |
| Mo | 2 | 6 |
| Al | 3.0 | 6.0 |
| Ti | 3.5 | 5.0 |
| Ta | 2.0 | 4.0 |
| Nb | 1.0 | 3.0 |
| Zr | 0.0 | 0.10 |
| V | 0.0 | 3.0 |
| C | 0.0 | 0.20 |
| B | 0.0 | 0.10 |
| W | 0.0 | 1.0 |

In another of its broader aspects, objects of the invention can be achieved by providing a composition of the following approximate content:

| Ingredient | Concentration in Weight % Claimed Composition | |
| --- | --- | --- |
| | From | To |
| Ni | balance | |
| Co | 4 | 12 |
| Cr | 7 | 13 |
| Mo | 2 | 6 |
| Al | 3.0 | 6.0 |
| Ti | 3.5 | 5.0 |
| Ta | 2.0 | 4.0 |
| Nb | 1.0 | 3.0 |
| Re | 0.0 | 3.0 |
| Hf | 0.0 | 0.75 |
| Zr | 0.0 | 0.10 |
| V | 0.0 | 3.0 |
| C | 0.0 | 0.20 |
| B | 0.0 | 0.10 |
| W | 0.0 | 1.0 |
| Y | 0.0 | 0.10 |

BRIEF DESCRIPTION OF THE DRAWINGS

In the description which follows clarity of understanding will be gained by reference to the accompanying drawings in which.

DETAILED DESCRIPTION OF THE INVENTION

Figure 1:
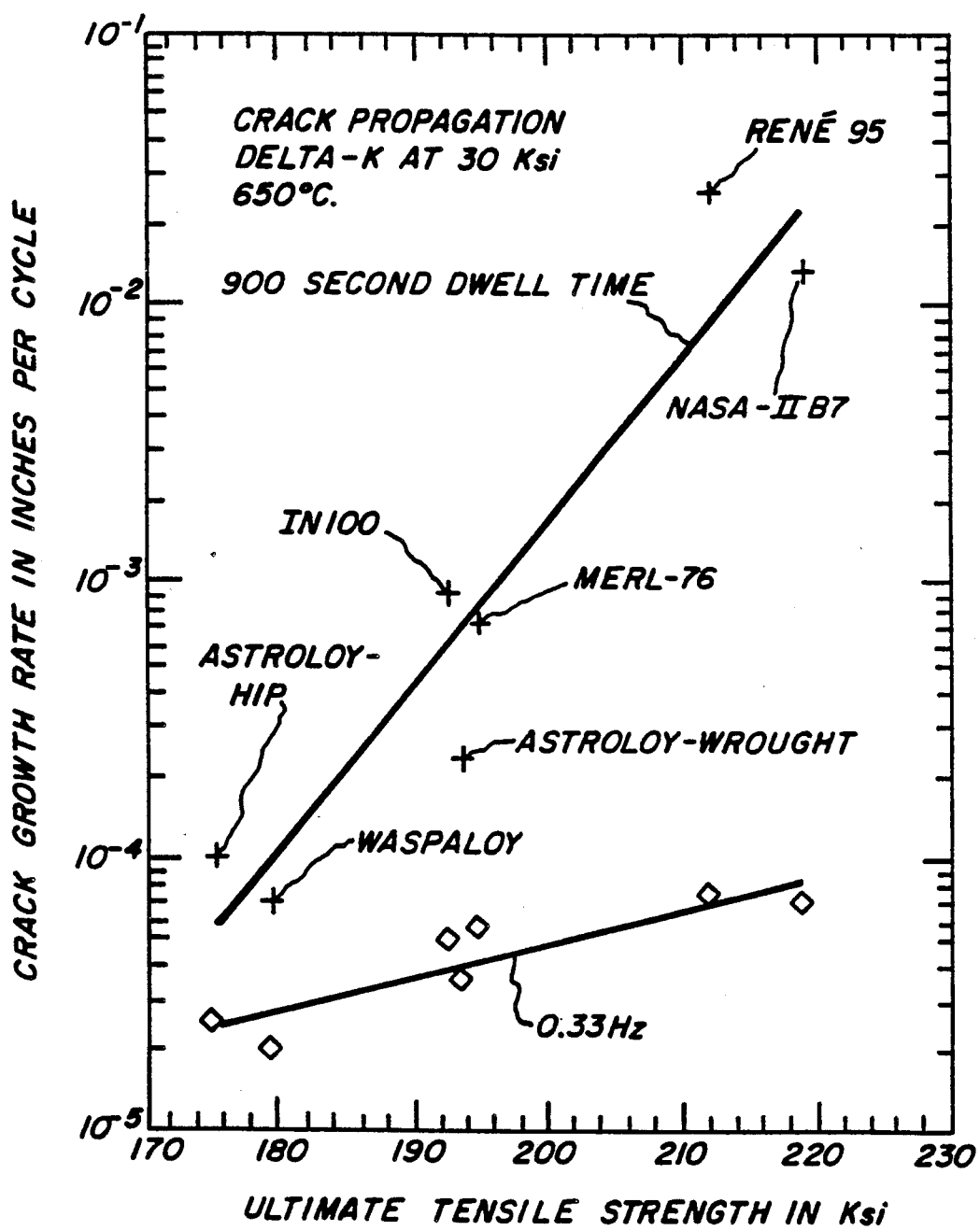
FIG. 1 is a graph in which fatigue crack growth in inches per cycle is plotted on a log scale against ultimate tensile strength in ksi.

I have discovered that by studying the present commercial alloys employed in structures which required high strength at high temperature that the conventional super-alloys fall into a pattern. This pattern is based on plotting in a manner which I have devised of data appearing in the Final Report NASA CR-165123 referenced above. I plotted the data from the NASA report of 1980 with the parameters arranged as indicated in FIG. 1. There is a generally diagonally arrayed display of data points evident from a study of FIG. 1 of the drawings.

In FIG. 1, the crack growth rate in inches per cycle is plotted against the ultimate tensile strength in ksi. The individual alloys are marked on the graph by plus signs which identify the respective crack growth rate in inches per cycle characteristic of the alloy at an ultimate tensile strength in ksi which is correspondingly also characteristic for the labeled alloy. As will be observed, a line identified as a 900 second dwell time plot shows the characteristic relationship between the crack growth rate and the ultimate tensile strength for these conventional and well known alloys. Similar points corresponding to those of the labeled pluses are shown at the bottom of the graph for crack propagation rate tests conducted at 0.33 Hertz or in other words, at a higher frequency. A diamond data point appears in the region along the line labeled 0.33 Hertz for each labeled alloy shown in the upper part of the graph.

From FIG. 1, it became evident that there is no alloy composition, which had coordinates of FIG. 1, which fell in the lower right hand corner of the graph for long dwell time. In fact, since all of the data points for the longer dwell time crack growth testing fell along the diagonal line of the graph, it appeared possible that any alloy composition which was formed would fall somewhere along the diagonal line of the graph. In other words, it appeared that it was possible that no alloy composition could be found which had both a high ultimate tensile strength and a low crack growth rate at long dwell times according to the parameters plotted in FIG. 1.

However, I have found that it is possible to produce an alloy which has a composition which permits the unique combination of high ultimate strength and low crack growth rate to be achieved.

Figure 2:
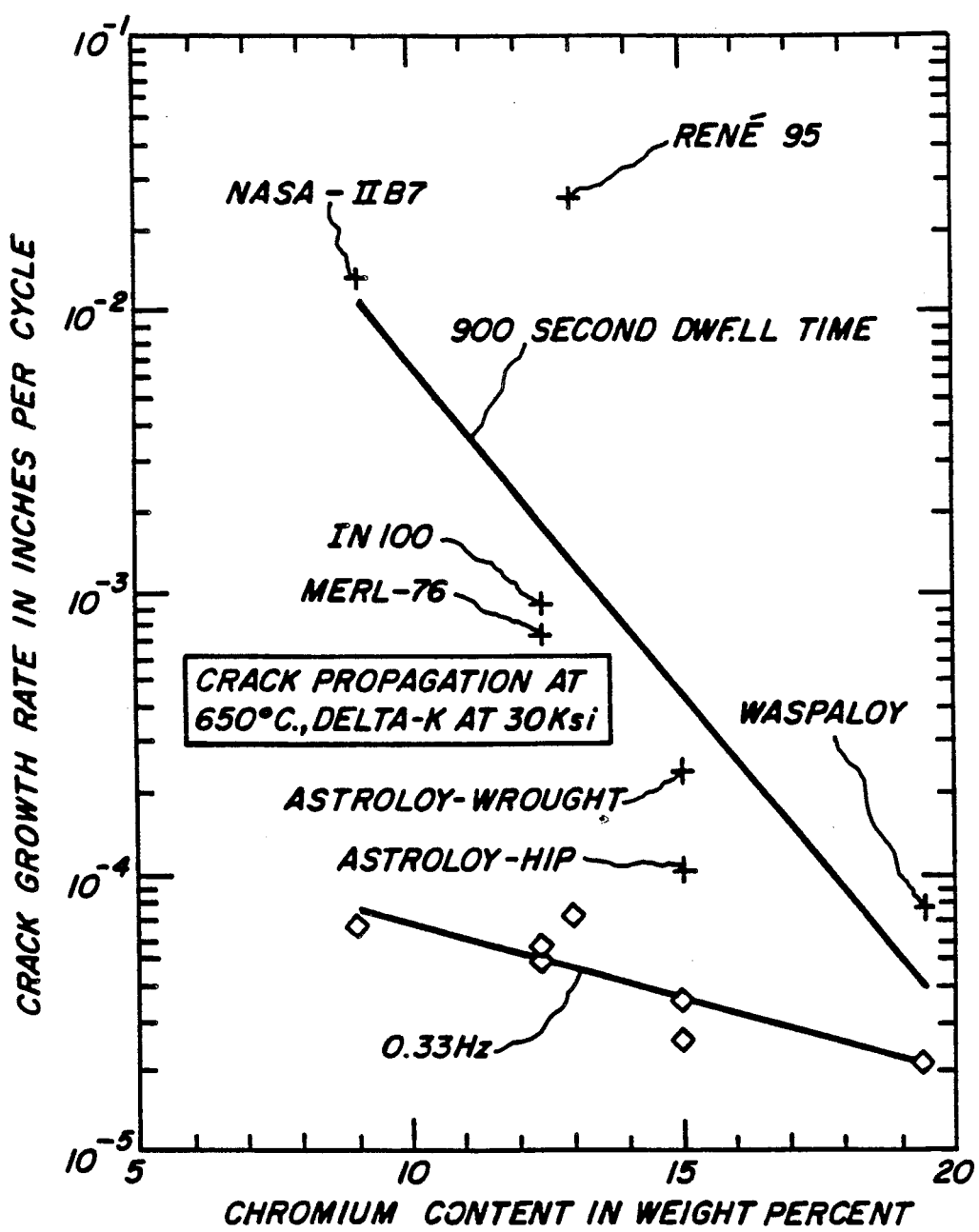
FIG. 2 is a plot similar to that of FIG. 1 but having an abscissa scale of chromium content in weight %.

One of the conclusions which I reached on a tentative basis regarding the data plotted in FIG. 1 was that there may be some influence of the chromium concentration on the crack growth rate of the various alloys. For this reason, and using data from the 1980 NASA report, I plotted the chromium content in weight % against the crack growth rate and the results of this plot is shown in FIG. 2. In this figure, the chromium content is seen to vary between about 9 to 19% and the corresponding crack growth rate measurements indicate that as the chromium content increases, in general, the crack growth rate decreases. Based on this graph, it appeared that it might be very difficult or impossible to devise an alloy composition which had a low chromium content and also had a low crack growth rate at long dwell times.

However, I have found that it is possible through proper alloying of the combined ingredients of a superalloy compositions to form a composition which has both a low chromium content and a low crack growth rate at long dwell times.

Figure 3:
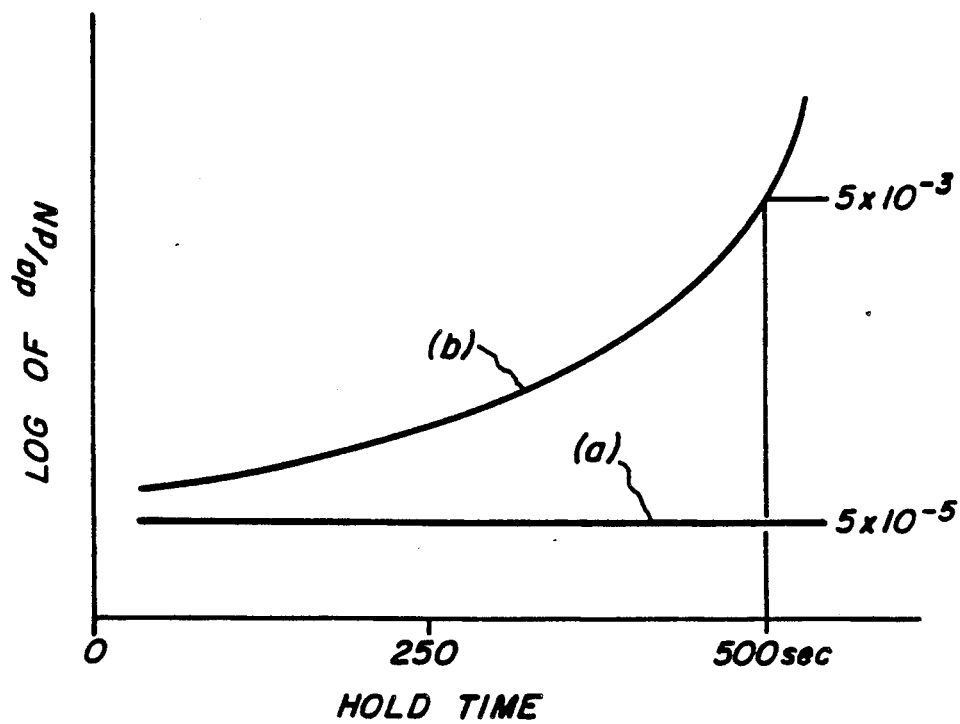
FIG. 3 is a plot of the log of crack growth rate against the hold time in seconds for a cyclic application of stress to a test specimen.

One way in which the relationship between the hold time for subjecting a test specimen to stress and the rate at which crack growth varies, is shown in FIG. 3. In this figure, the log of the crack growth rate is plotted as the ordinate and the dwell time or hold time in seconds is plotted as the abscissa. A crack growth rate of $5 \times 10^{-5}$ might be regarded as an ideal rate for cyclic stress intensity factors of 25 ksi/in. If an ideal alloy were formed the alloy would have this rate for any hold time during which the crack or the specimen is subjected to stress. Such a phenomenon would be represented by the line (a) of FIG. 3 which indicates that the crack growth rate is essentially independent of the hold or dwell time during which the specimen is subjected to stress.

By contrast a non-ideal crack growth rate but one which actually conforms more closely to the actual phenomena of cracking is shown in FIG. 3 by the line plotted as line (b). For very short hold time periods of a second or a few seconds, it is seen that the ideal line (a) and the practical line (b) are separated by a relatively small amount. At these high frequencies, or low hold time, stressing of the sample the crack growth rate is relatively low.

However, as the hold time during which stress is applied to a sample is increased, the results which are obtained from experiments for conventional alloys follow the line (b). Accordingly it will be seen that there is an increase at greater than a linear rate as the frequency of the stressing is decreased and the hold time for the stressing is increased. At an arbitrarily selected hold time of about 500 seconds, it may be seen from FIG. 3 that a crack growth rate may increase by two orders of magnitude from $5 \times 10^{-5}$ to $5 \times 10^{-3}$ above the standard rate of $5 \times 10^{-5}$.

Again, it would be desirable to have a crack growth rate which is independent of time and this would be represented ideally by the path of the line (a) as the hold time is increased and the frequency of stress application is decreased.

Remarkably, I have found that by making slight changes in the ingredients of superalloys it is possible to greatly improve the resistance of the alloy to long dwell time crack growth propagation. In other words it has been found possible to reduce the rate of crack growth by alloying modification of the alloys. Further increase can be obtained as well by the treatment of the alloy. Such treatment is principally a thermal treatment.

EXAMPLE 1

An alloy identified as HK104 was prepared. The composition of the alloy was essentially as follows:

| Ingredient | Concentration in Weight % |
| --- | --- |
| Ni | balance |
| Co | 8 |
| Cr | 10 |
| Mo | 4 |
| Al | 4.5 |
| Ti | 4.0 |
| Ta | 3.0 |
| Nb | 1.5 |
| Re | 0.0 |
| Hf | 0.0 |
| Zr | 0.06 |
| V | 1.0 |
| C | 0.05 |
| B | 0.03 |
| Y | 0.0 |

The alloy was subjected to various tests and the results of these tests are plotted in the FIGS. 4 through 8. Herein alloys are identified by an appendage "-SS" if the data that were taken on the alloy were taken on material processed "super-solvus", i.e. the high temperature solid state heat treatment given to the material was at a temperature above which the strengthening precipitate ' .'' dissolves and below the incipient melting point. This usually results in grain size coarsening in the material. The strengthening phase ' .'' re-precipitates on subsequent cooling and aging.

Figure 4:
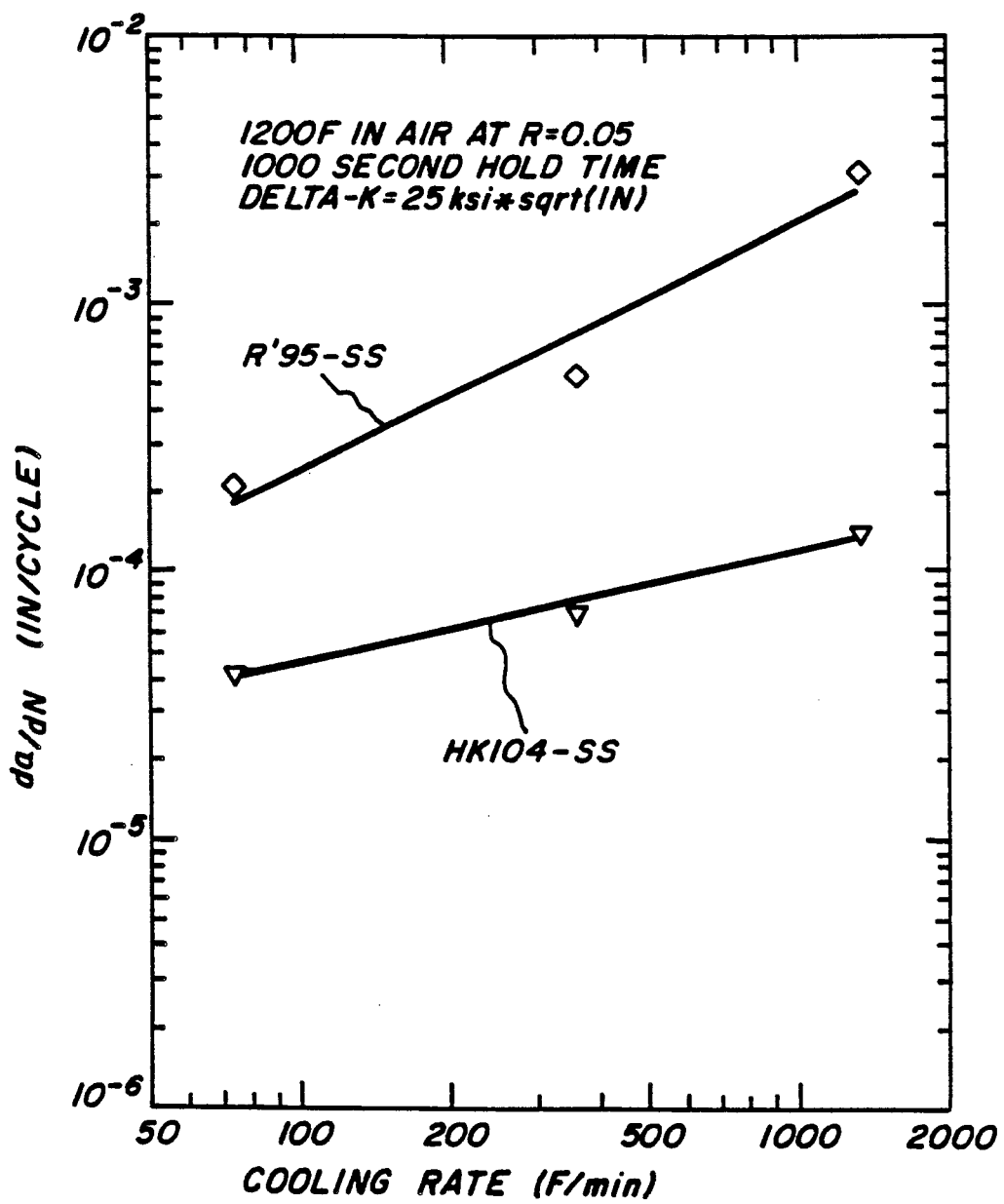
FIG. 4 is a graph in which the crack propagation rate, da/dN, in inches per cycle is plotted against the cooling rate in degrees Farenheit per minute.

Turning now to FIG. 4, the rate of crack propagation in inches per cycle is plotted against the cooling rate in ° F. per minute. The samples of Rene' 95-SS and HK104-SS were tested in air at 1200° F. with a 1000 second hold time at maximum stress intensity factor. As is evident, the HK104-SS has a lower crack growth rate than the Rene' 95-SS for samples cooled at all rates tried and that the HK104-SS cracks grow 4 to 20 times slower. It should be noted that a range of cooling rates for manufactured components from such superalloys is expected to be in the range of 100° F./min to 600° F./min.

Regarding the other properties of the alloy, they are described here with reference to the FIGS. 5, 6, 7 and 8.

The alloy of Example 1 is similar in certain respects to IN100 but comparative testing of the subject alloy and samples of Rene' g5-SS were carried out to provide a basis for comparing the subject alloy to an alloy much stronger than IN100. Test results obtained at 750° F. are plotted in FIGS. 5 and 6 and test results obtained at 1400° F. are plotted in FIGS. 7 and 8.

Figure 5:
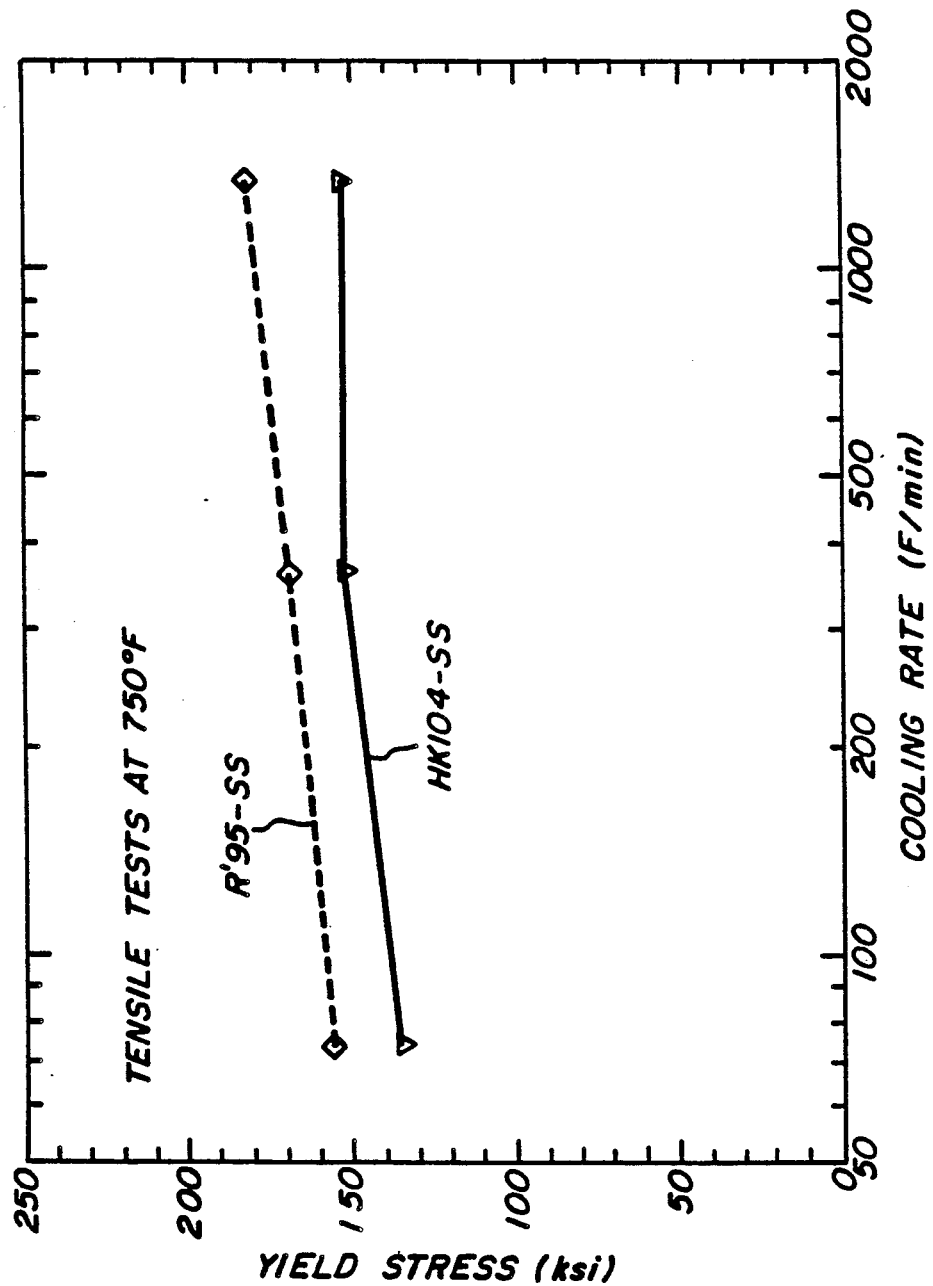
FIG. 5 is a graph of the yield stress in ksi at 750° F. plotted against cooling rate in degrees Farenheit per minute on a log scale.

Reference is made first to the test data plotted in FIG. 5. In FIG. 5, there is plotted a relationship between the yield stress in ksi and the cooling rate in ° F. per minute for two alloy samples, HK104-SS and Rene' 95-SS tests on which were performed at 750° F. In this plot there is evidence of that the HK104-SS alloy is only 10 to 16% lower in yield strength at 750° F. than R'95-SS, an alloy well-known for its high strength.

The samples of HK104-SS and Rene' 95-SS were both prepared by powder metallurgy techniques and are accordingly quite comparable to each other.

Figure 6:
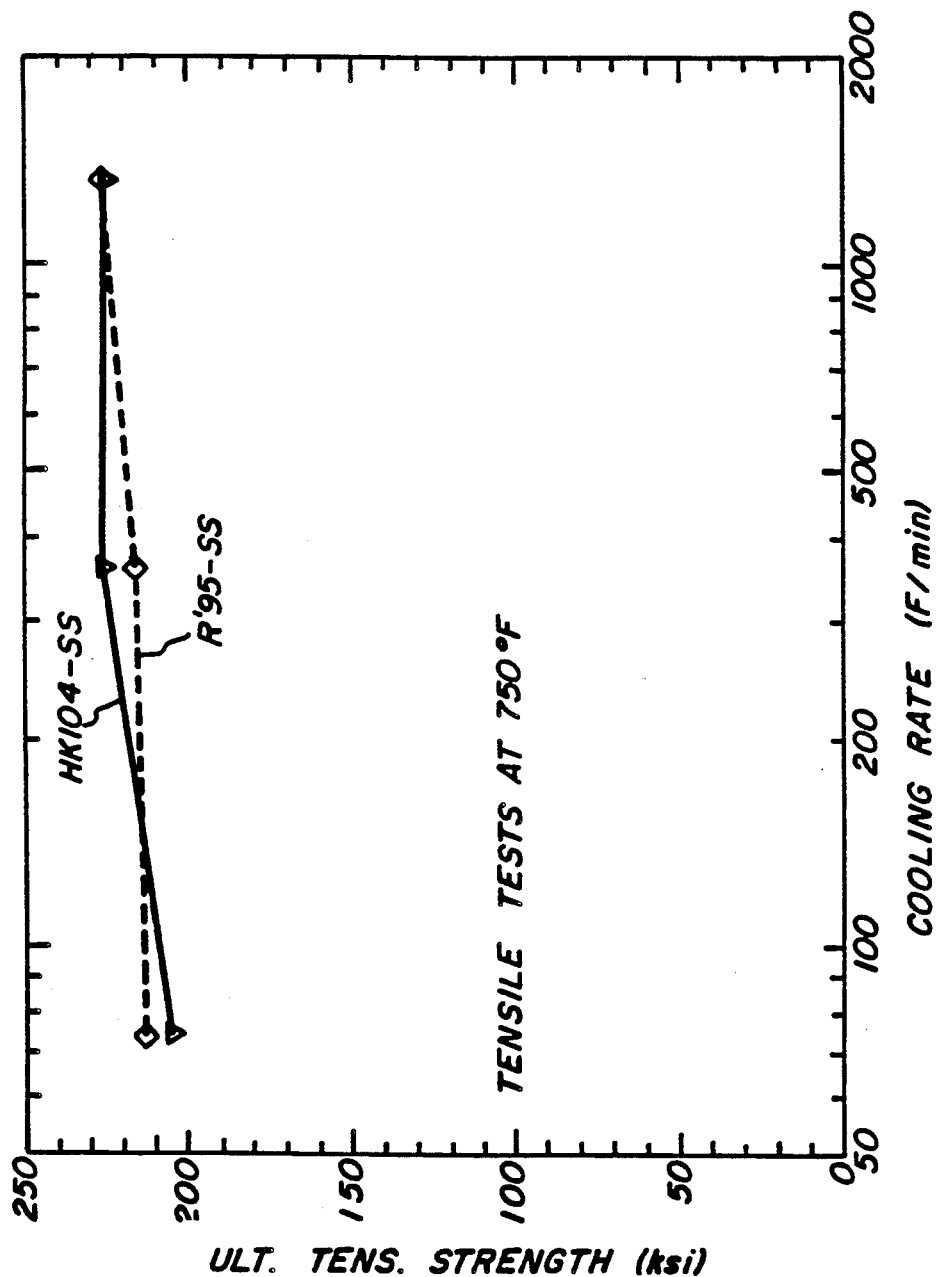
FIG. 6 is a graph of the ultimate tensile strength in ksi at 750° F. plotted against the cooling rate in degrees Farenheit per minute on a log scale.

In FIG. 6, a plot is set forth of ultimate tensile strength in ksi against the cooling rate in ° F. per minute for a sample prepared according to the above example of alloy HK104-SS and also by way of comparison, a sample of Rene' 95-SS. The samples tested were measured at 750° F. It is well-known that Rene' 95 is one of the strongest commercially availale superalloys which is known. From FIG. 6, it is evident that the ultimate tensile strength measurements made on the respective samples of the HK104-SS alloy and the Rene' 95-SS alloy demonstrated that the HK104-SS alloy indeed has ultimate tensile strength which is essentially equivalent to the Rene' 95-SS material.

Figure 7:
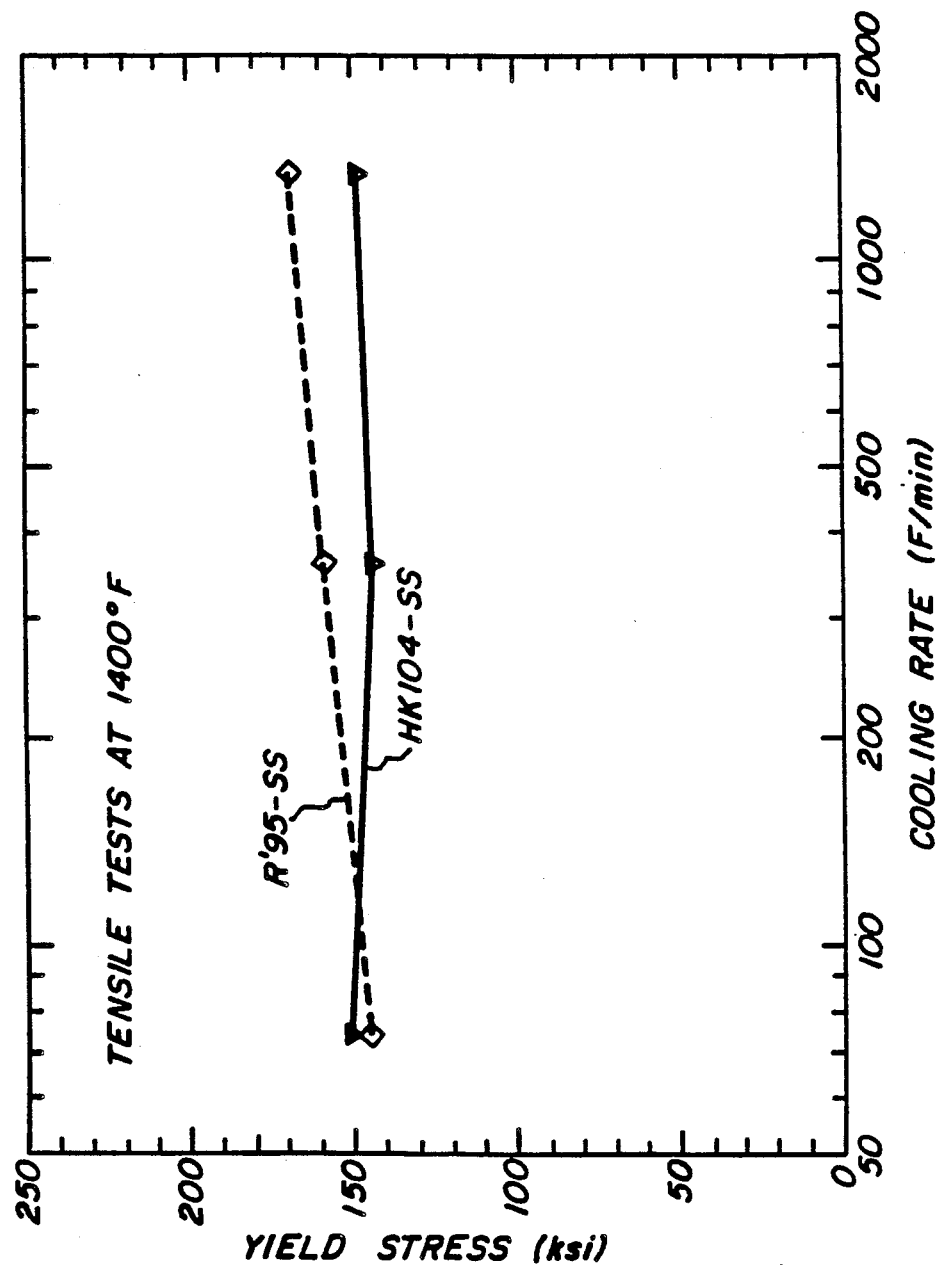
FIG. 7 is a graph of the yield stress in ksi at 1400° F. plotted against the cooling rate in degrees Farenheit per minute.
Figure 8:
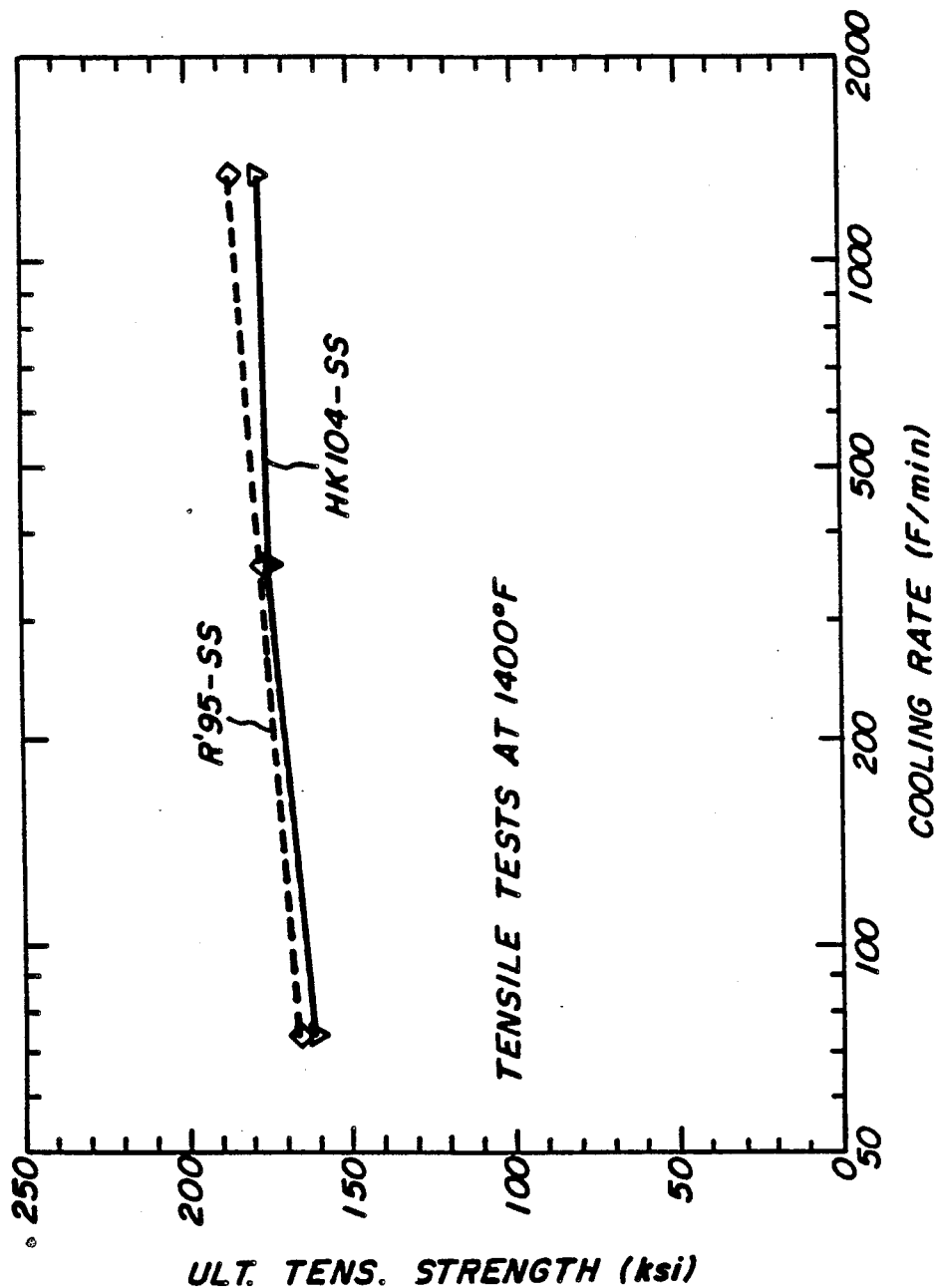
FIG. 8 is a graph of the ultimate tensile strength in ksi at 1400° F. plotted against the cooling rate in degrees Farenheit per minute.

Turning now to FIGS. 7 and 8, there is plotted the relationship between the yield strength and ultimate tensile at 1400° F. versus the cooling rate in ° F. per minute for two alloys, one being Rene' 95-SS and the other being HK104-SS both of which samples were tested at 1400° F. At most HK104-SS is only 12% lower than Rene' 95-SS at higher cooling rates and essentially equivalent to Rene' 95-SS at lower cooling rates for yield stress, and essentially equivalent to Rene' 95-SS for ultimate tensile strength.

Additionally, the ultimate tensile strength of 212 ksi measured at 1200° F. (649° C.) on material cooled at 360° F./min demonstrates a remarkable improvement over the powder metallurgy IN100 of FIG. 1.

Moreover, with respect to inhibition of fatigue crack propagation the subject alloys are far superior to Rene' 95 particularly those alloys prepared at cooling rates of 100° F./min to 600° F./min which are the rates which are to be used for industrial production of the subject alloy.

EXAMPLE 2

An alloy identified as HK103 was prepared. The composition of the alloy was essentially as follows:

| Ingredient | Concentration in Weight % |
| --- | --- |
| Ni | balance |
| Co | 8 |
| Cr | 10 |
| Mo | 4 |
| Al | 4.8 |
| Ti | 4.2 |
| Ta | 3.0 |
| Nb | 1.5 |
| Re | 0.0 |
| Hf | 0.0 |
| Zr | 0.06 |
| V | 0.0 |
| C | 0.05 |
| B | 0.03 |
| Y | 0.0 |

The alloy was subjected to various tests and the results of these tests are plotted in the FIGS. 9 through 13. As previously stated, alloys are identified herein by an appendage "-SS" if the data that were taken on the alloy were taken on material processed "super-solvus", i.e. the high temperature solid state heat treatment given to the material was at a temperature above which the strengthening precipitate $\gamma'$ dissolves and below the incipient melting point. The strengthening phase $\gamma'$ re-precipitates on subsequent cooling and aging.

Figure 9:
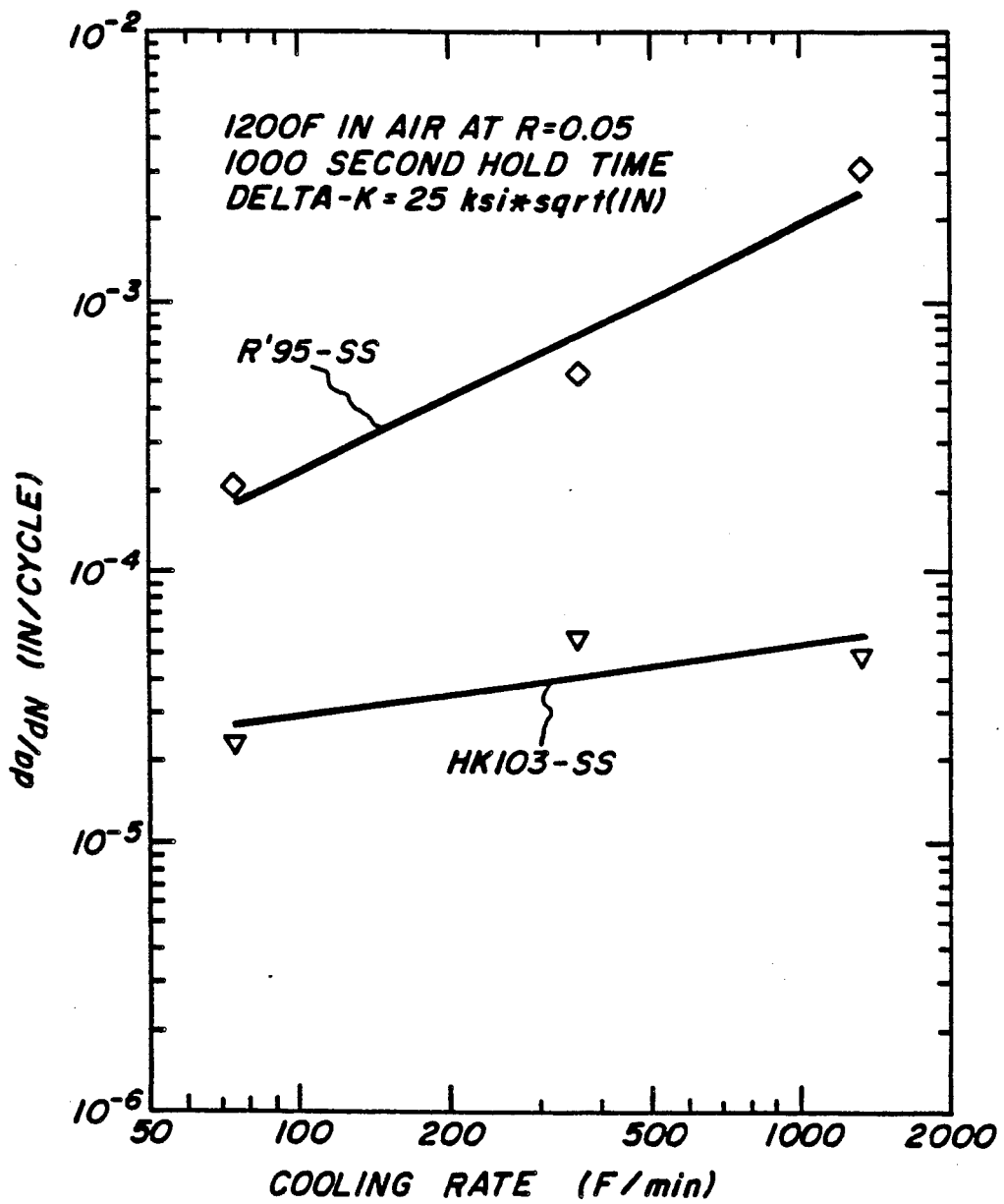
FIG. 9 is a second graph in which the crack propagation rate, da/dN, in inches per cycle is plotted against the cooling rate in degrees Farenheit per minute.

Turning now to FIG. 9, the rate of crack propagation in inches per cycle is plotted against the cooling rate in ° F. per minute. The samples of Rene' 95-SS and HK103-SS were tested in air at 1200° F. with a 1000 second hold time at maximum stress intensity factor. As is evident, the HK103-SS has a lower crack growth rate than the Rene' 95-SS for samples cooled at all rates tried and that the HK103-SS cracks grow 8 to 60 times slower. As noted above, a range of cooling rates for manufactured components from such superalloys is expected to be in the range of 100° F./min to 600° F./min.

Regarding the other properties of the subject alloy, they are described here with reference to the FIGS. 10, 11, 12 and 13.

The alloy of Example 2 is also similar in certain respects to IN100 and comparative testing of the subject alloy and samples of Rene' 95-SS were carried out to provide an additional basis for comparing the subject alloy to an alloy much stronger than IN100. Test results obtained at 750° F. are plotted in FIGS. 10 and 11 and test results obtained at 1400° F. are plotted in FIGS. 12 and 13.

Figure 10:
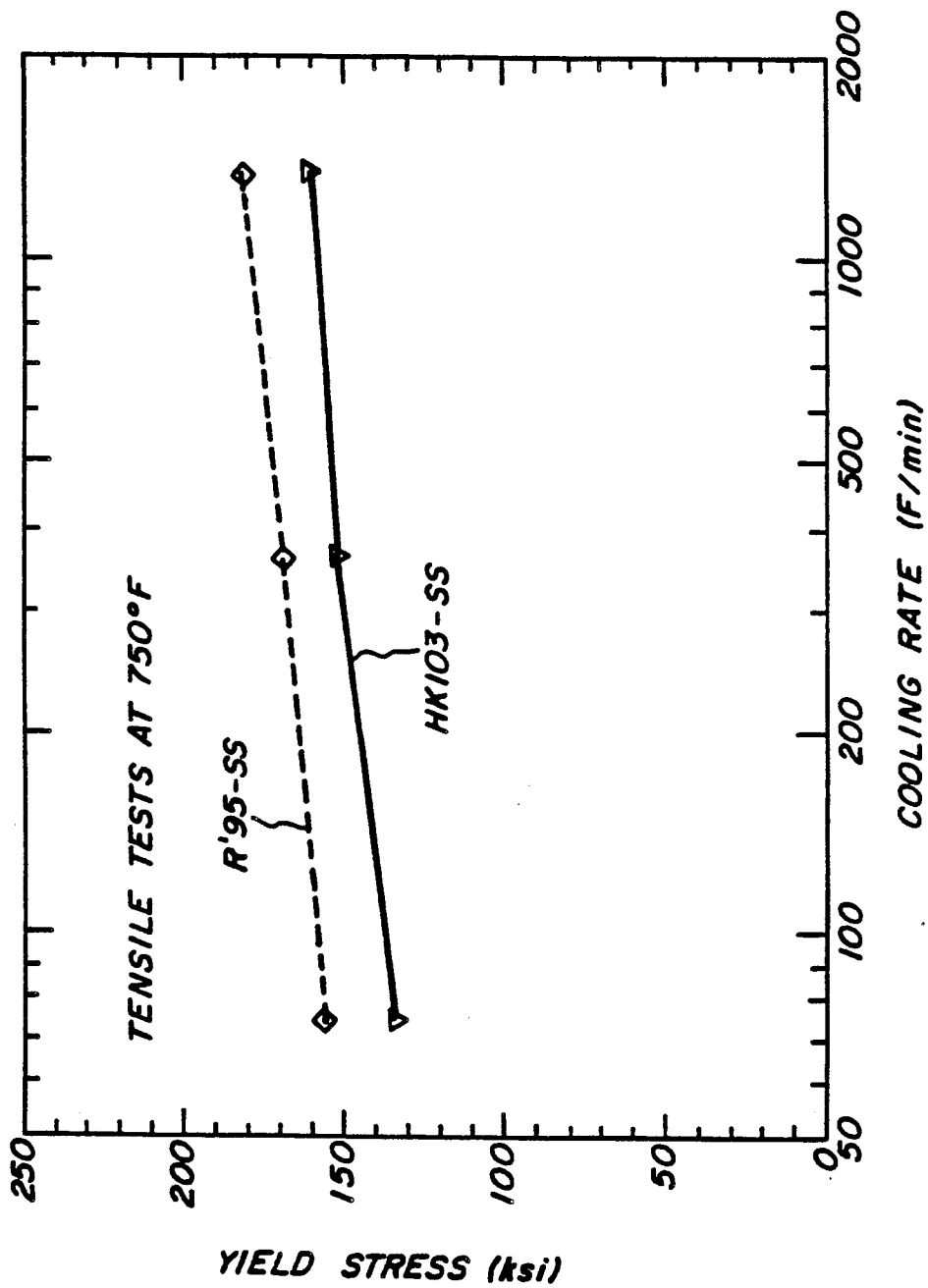
FIG. 10 is a second graph of the yield stress in ksi at 750° F. plotted against cooling rate in degrees Farenheit per minute on a log scale.

Reference is made first to the test data plotted in FIG. 10. In FIG. 10, there is plotted a relationship between the yield stress in ksi and the cooling rate in ° F. per minute for two alloy samples, HK103-SS and Rene' 95-SS, tests on which were performed at 750° F. In this plot, there is evidence that the HK103-SS alloy is only 12 to 14% lower in yield strength at 750° F. than Rene' 95-SS, an alloy well-known for its high strength.

As in the case of the HK104-SS alloy, the samples of HK103-SS and Rene' 95-SS were both prepared by powder metallurgy techniques and are, accordingly, quite comparable to each other.

Figure 11:
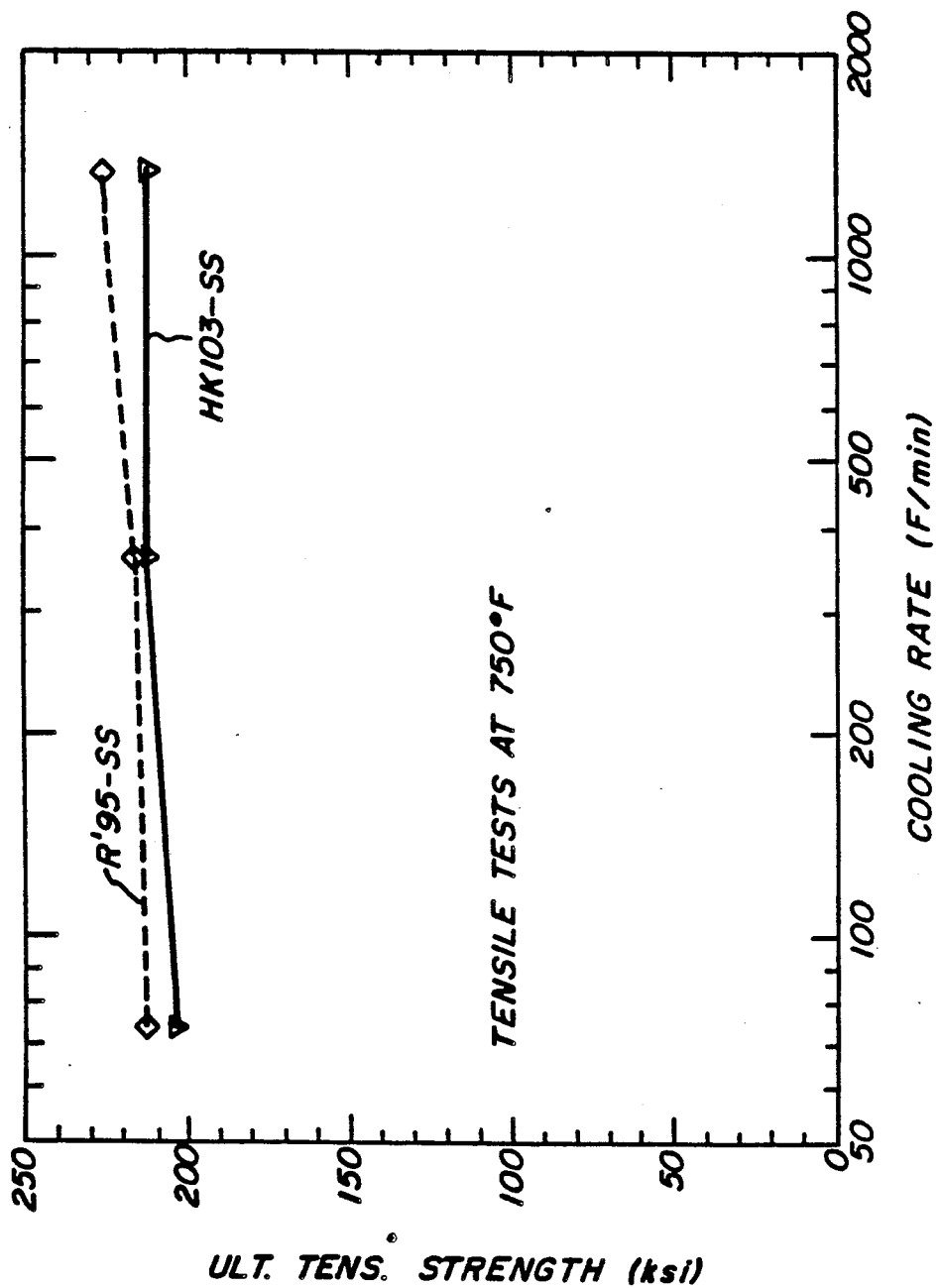
FIG. 11 is a second graph of the ultimate tensile strength in ksi at 750° F. plotted against the cooling rate in degrees Farenheit per minute on a log scale.

In FIG. 11, a plot is set forth of ultimate tensile strength in ksi against the cooling rate in ° F. per minute for a sample prepared according to the above example of alloy HK103-SS and also by way of comparison, a sample of Rene' 95-SS The samples tested were measured at 750° F. It is well-known that Rene' 95 is one of the strongest commercially available superalloys which is known. From FIG. 11, it is evident that the ultimate tensile strength measurements made on the respective samples of the HK103-SS alloy and the Rene' 95-SS alloy demonstrated that the HK103-SS alloy indeed has ultimate tensile strength which is closely comparable to the Rene' 95-SS material.

Figure 12:
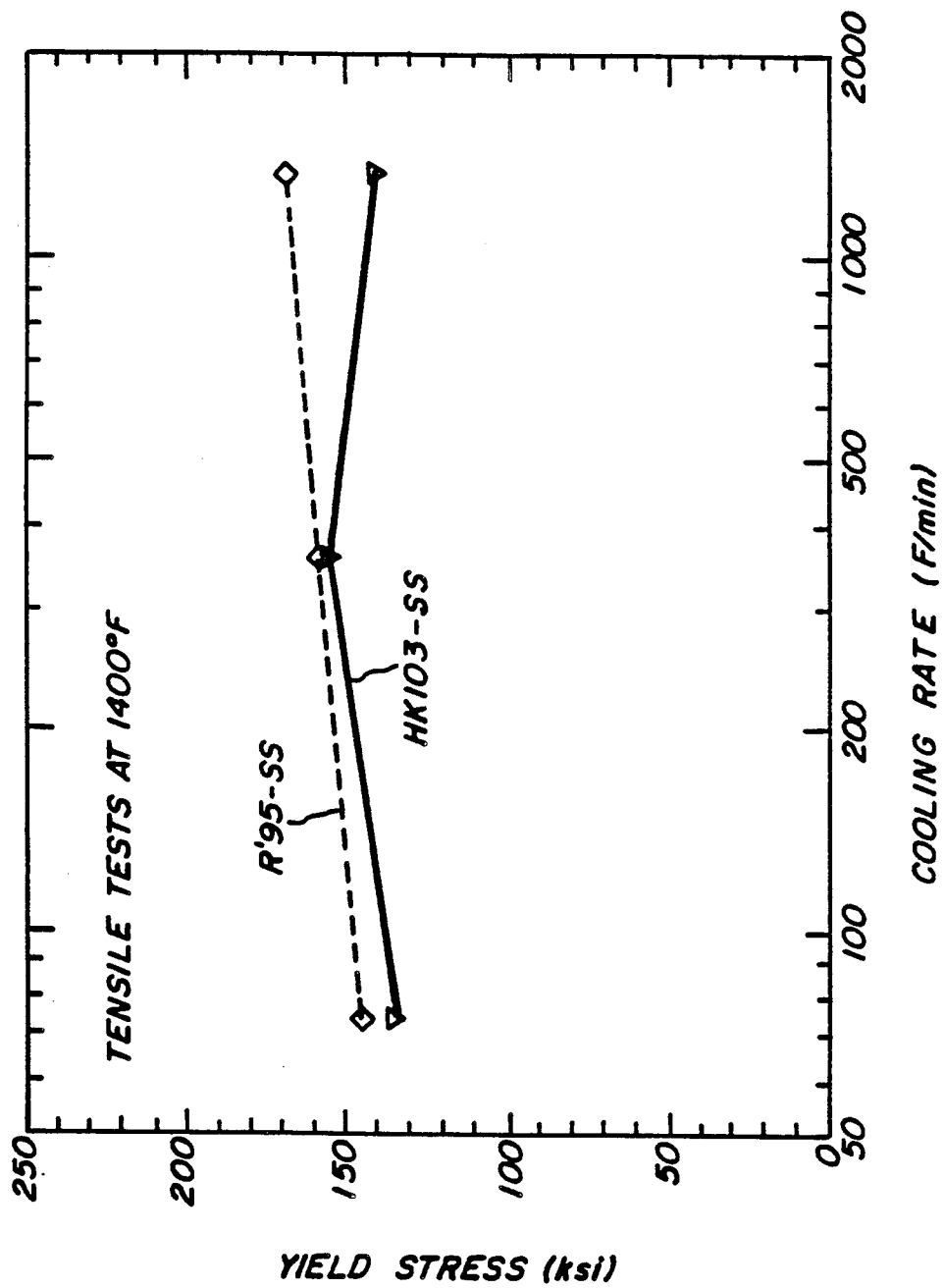
FIG. 12 is a second graph of the yield stress in ksi at 1400° F. plotted against the cooling rate in degrees Farenheit per minute.
Figure 13:
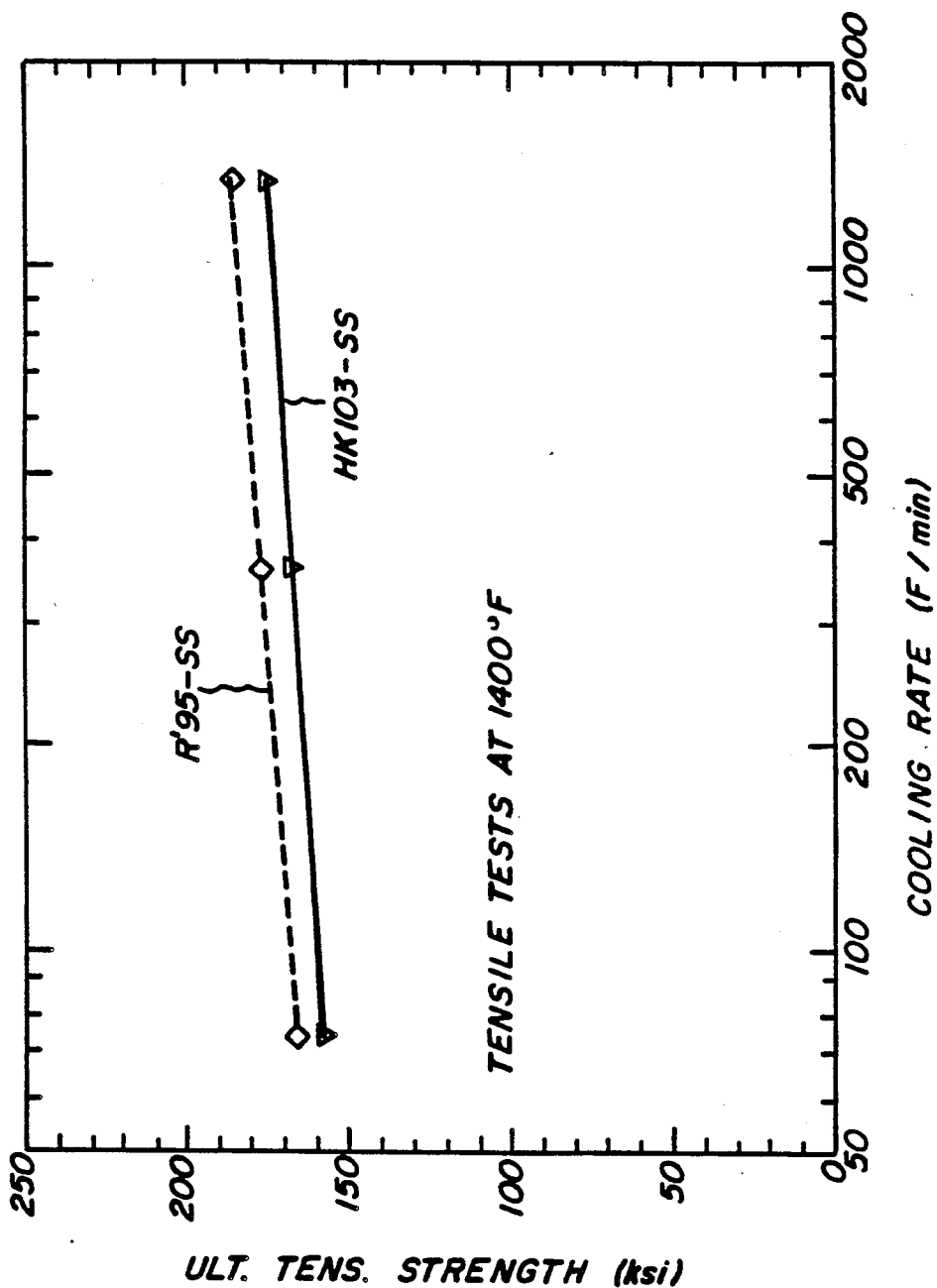
FIG. 13 is a second graph of the ultimate tensile strength in ksi at 1400° F. plotted against the cooling rate in degrees Farenheit per minute.

Turning now to FIGS. 12 and 13, there is plotted the relationship between the yield strength and ultimate tensile at 1400° F. versus the cooling rate in ° F. per minute for two alloys, one being Rene' 95-SS and the other being HK103-SS, both of which samples were tested at 1400° F. At most, HK103-SS is only 16% lower than Rene' 95-SS at higher cooling rates and closely comparable to Rene' 95-SS at lower cooling rates for yield stress and only slightly below Rene' 95-SS for ultimate tensile strength.

From the foregoing, it is evident that the invention provides alloys having unique combinations of ingredients based both on the ingredient identification and on the relative concentrations thereof. It is also evident that the alloys which are proposed pursuant to the present invention have a novel and unique capability for crack propagation inhibition. The low crack propagation rates, da/dN, for the HK103-SS and HK104-SS alloys which are evident from FIGS. 4 and 9 is a uniquely novel and remarkable result.

This is quite surprising inasmuch as the constituents of the subject alloys are only slightly different from constituents found in IN100 alloy although the slight difference is critically important in yielding dramatic differences, and specifically improvements in strength without an increase in crack propagation rates at long cycle fatigue tests. It is this slight difference in ingredients and proportions which results in the surprising and unexpectedly low fatigue crack propagation rates coupled with a highly desirable set of strength and other properties as also evidenced from the graphs of the figures of the subject application.

What is remarkable about the achievement of the present invention is the striking improvement which has been made in fatigue crack propagation resistance with a relatively small change in ingredients of the HK104 and HK103 alloys as compared to those of the IN100 alloy.

To illustrate the small change in alloy compositions the ingredients of the IN100 and of both the HK104 and HK103 alloys are listed here.

TABLE I

| Ingredient | HK103 | HK104 | IN100 |
|---|---|---|---|
| Ni | 64.36 | 63.86 | 60.68 |
| Co | 8 | 8 | 15 |
| Cr | 10 | 10 | 10 |
| Mo | 4 | 4 | 3.0 |
| Al | 4.8 | 4.5 | 5.5 |
| Ti | 4.2 | 4.0 | 4.7 |
| Ta | 3.0 | 3.0 | — |
| Nb | 1.5 | 1.5 | — |
| Zr | 0.06 | 0.06 | 0.06 |
| C | 0.05 | 0.05 | 0.01 |
| B | 0.03 | 0.03 | 0.01 |
| V | 0.0 | 1.0 | 1.0 |

From the above Table I, it is evident that the significant differences between the composition of IN100 alloy as compared to that of alloy HK104 is that the subject alloy omits 7.0 weight percent cobalt, 1.0 weight percent aluminum, and 0.70 weight percent titanium, and adds 3.0 weight percent tantalum, 1.5 weight percent niobium and 1.0 weight percent molybdenum.

With reference to the HK103 alloy, it differs from the HK104 alloy only in having a higher aluminum (4.8 vs. 4.5 for HK104), a higher titanium (4.2 vs. 4.0 for HK104) and lower vanadium (0.0 vs. 1.0 for HK104). The comparison between HK104 and IN100 applies to the HK103 alloy except in these three respects.

It is deemed rather remarkable considering the teachings of FIG. 1 that this alteration of the composition can accomplish an increase or improvement of the basic strength properties of the alloy almost up to that of Rene' 95 and at the same time provide long dwell time fatigue crack inhibition of the alloy. However, this is precisely the result of the alteration of the composition as is evidenced by the data which is given in the figures and discussed extensively above.

Other changes in ingredients may be made which do not cause such remarkable change of properties, particularly smaller changes of some ingredients. For example, small additions of rhenium may be made to the extent that they do not change, and parlticularly do not detract from, the uniquely beneficial combination of properties which have been found for the HK104 and HK103 alloys.

While the alloy is described above in terms of the ingredients and percentages of ingredients which yield uniquely advantageous proportions, particularly with respect to inhibition of crack propagation it will be realized that other ingredierfts such as yttrium, hafnium, etc., can be included in the composition in percentages which do not interfere with the novel crack propagation inhibition. A small percentage of yttrium between 0 and 0.1 percent may be included in the subject alloy without detracting from the unique and valuable combination of properties of the subject alloy.

What is claimed is:

1. As a composition of matter an alloy having a high strength and having a substantially lower crack propagation rate, said alloy consisting essentially of the following ingredients in the following proportions:

| Ingredient | Concentration in Weight % Claimed Composition | |
|---|---|---|
| | From | To |
| Ni | balance | |
| Co | 4 | 12 |
| Cr | 7 | 13 |
| Mo | 2 | 6 |
| Al | 3.0 | 6.0 |
| Ti | 3.5 | 5.0 |
| Ta | 2.0 | 4.0 |
| Nb | 1.0 | 3.0 |
| Re | 0.0 | 3.0 |
| Hf | 0.0 | 0.75 |
| Zr | 0.00 | 0.10 |
| V | 0.0 | 3.0 |
| C | 0.0 | 0.20 |
| B | 0.01 | 0.10 |
| W | 0.0 | 1.0 |
| Y | 0.0 | 0.1 |

2. As a composition of matter an alloy having a high strength and having a substantially lower crack propagation rate, said alloy consisting essentially of the following ingredients in the following proportions:

| Ingredient | Concentration in Weight % Claimed Composition |
|---|---|
| Ni | balance |
| Co | 8 |
| Cr | 10 |
| Mo | 4 |
| Al | 4.5 |
| Ti | 4.0 |
| Ta | 3.0 |
| Nb | 1.5 |
| Zr | 0.06 |
| C | 0.05 |
| B | 0.03 |
| V | 1.0 |

3. As a composition of matter an alloy having a high strength and having a substantially lower crack propagation rate, said alloy consisting essentially of the following ingredients in the following proportions:

| Ingredient | Concentration in Weight % Claimed Composition |
|---|---|
| Ni | balance |
| Co | 8 |
| Cr | 10 |
| Mo | 4 |
| Al | 4.8 |
| Ti | 4.2 |
| Ta | 3.0 |
| Nb | 1.5 |
| Zr | 0.06 |
| C | 0.05 |
| B | 0.03 |

* * * * *